(12) United States Patent
Bukhman

(10) Patent No.: US 9,220,432 B2
(45) Date of Patent: Dec. 29, 2015

(54) METHOD AND SYSTEM OF UTILIZING ECG SIGNAL FOR CENTRAL VENOUS CATHETER TIP POSITIONING

(71) Applicant: C. R. Bard, Inc., Murray Hill, NJ (US)

(72) Inventor: Vladislav Bukhman, East Northport, NY (US)

(73) Assignee: C. R. Bard, Inc., Murray Hill, NJ (US)

( * ) Notice: Subject to any disclaimer, the term of this patent is extended or adjusted under 35 U.S.C. 154(b) by 266 days.

(21) Appl. No.: 13/844,755

(22) Filed: Mar. 15, 2013

(65) Prior Publication Data

US 2014/0249505 A1 Sep. 4, 2014

Related U.S. Application Data

(60) Provisional application No. 61/771,825, filed on Mar. 2, 2013.

(51) Int. Cl.
| | | |
|---|---|---|
| *A61B 5/06* | (2006.01) | |
| *A61M 25/01* | (2006.01) | |
| *A61B 5/042* | (2006.01) | |
| *A61B 19/00* | (2006.01) | |

(52) U.S. Cl.
CPC .............. *A61B 5/042* (2013.01); *A61B 5/065* (2013.01); *A61B 19/5244* (2013.01); *Y02E 10/549* (2013.01)

(58) Field of Classification Search
CPC ........ A61B 5/06; A61B 5/065; A61B 5/0245; A61B 8/42
See application file for complete search history.

(56) References Cited

U.S. PATENT DOCUMENTS

| | | | |
|---|---|---|---|
| 2005/0010120 A1* | 1/2005 | Jung et al. | 600/509 |
| 2008/0234978 A1 | 9/2008 | Neumann et al. | |
| 2009/0259124 A1 | 10/2009 | Rothenberg | |
| 2009/0275827 A1* | 11/2009 | Aiken et al. | 600/424 |
| 2010/0261977 A1 | 10/2010 | Seely | |
| 2010/0317981 A1 | 12/2010 | Grunwald | |
| 2011/0028856 A1* | 2/2011 | Zhang | 600/515 |
| 2012/0136242 A1* | 5/2012 | Qi et al. | 600/424 |
| 2013/0296725 A1* | 11/2013 | Lee et al. | 600/509 |

FOREIGN PATENT DOCUMENTS

WO 2014137841 A1 9/2014

OTHER PUBLICATIONS

PCT/US2014/019664 filed Feb. 28, 2014 International Search Report and Written Opinion dated May 30, 2014.

* cited by examiner

*Primary Examiner* — Christopher D Koharski
*Assistant Examiner* — Natasha Patel
(74) *Attorney, Agent, or Firm* — Rutan & Tucker, LLP

(57) ABSTRACT

Disclosed herein are a method and a medical system for utilizing of a intravascular ECG signal for central venous catheter placement. The medical system is capable of detecting the position of a catheter tip and assessing its location relative to the cavoatrial junction. The detection and assessment are performed by a multiscale analysis of the complexity of the intravascular signal data points.

19 Claims, 8 Drawing Sheets

METHOD AND SYSTEM OF UTILIZING ECG SIGNAL FOR CENTRAL VENOUS CATHETER TIP POSITIONING

PRIORITY

This application claims the benefit of priority to U.S. Provisional Application No. 61/771,825, filed Mar. 2, 2013, which is incorporated by reference in its entirety into this application.

BACKGROUND

Various endovascular devices, including without limit central venous catheters ("CVC"), may be inserted into the vasculature of a patient to detect and/or treat various health issues. CVCs are endovascular devices including any catheter designed to utilize the central veins (e.g., subclavian and superior vena cava) or right sided cardiac chambers for the delivery and/or withdrawal of blood, blood products, therapeutic agents, and/or diagnostic agents. CVCs also include catheters inserted into the central veins or right sided cardiac chambers for the acquisition of hemodynamic data. Standard central venous catheters for intravenous access, dialysis catheters, percutaneously introduced central catheters ("PICC" lines), and right heart ("Swan-Ganz™") catheters are examples of CVCs. In some applications, an endovascular device, e.g., a central venous catheter (CVC), may be inserted into the superior vena cava (SVC) of a patient.

The specific location placement of an endovascular device is very important and can have a significant impact on the health of the patient. For example, a central venous catheter (CVC) with its tip located in the ideal position provides reliable vascular access with optimal therapeutic delivery, while minimizing short and long-term complications. In the United States, the ideal catheter tip placement of a CVC in the SVC is within 10 mm from the junction of the SVC and the right atrium (i.e., the "cavoatrial junction"). According to FDA, the tip of catheter tip should not be placed in, or allowed to enter, the right atrium of the heart. In 1989, the Food and Drug Administration issued a warning citing an increased risk of perforation of the right atrium, clot formation, and arrhythmias among other potential complications resulting from the tip of the CVC being placed inside the right atrium.

While CVCs have been used for many years, determining the position of the tip of the CVC has always been problematic. Further, in addition to the need to know where the tip is during initial placement, the CVC may migrate or otherwise move after the initial placement and require re-positioning. Therefore, the operator must monitor or periodically reevaluate the location of the tip.

Electrocardiogram (ECG) based guidance can be used as a positioning technique for catheter tip placement and confirmation. The electrical conduction system of the heart creates specific electrical signals, electrical energy distributions and behaviors thereof which are indicative of specific locations in the thoracic cavity and/or of specific heart functions or conditions. When measured endovascularly or intravascularly, i.e., from within blood vessels or from within the heart, certain parameters of the electrical activity of the heart can be used to identify specific locations in the cardiovascular system and/or functional conditions, normal or abnormal. An electrocardiogram (ECG) measures electrical potential changes occurring in the heart. The P wave portion of the ECG waveforms represents atrial muscle depolarization: the first half is attributable to the right atrium and the second half to the left atrium. Under normal circumstances, atrial muscle depolarization is initiated by a release of an excitatory signal from the sino-atrial node, a specialized strip of tissue located at the juncture of the superior vena cava ("SVC") and right atrium.

Some methods of ECG based guidance employ morphological and/or spectral analysis of ECG waveforms, specifically P waves, to position a catheter tip. (See Patent Application Publication U.S. 2010/0317981, which is incorporated by reference in its entirety into this application). Techniques of using ECG waveforms to locate the tip of a CVC have shown that both the magnitude and shape of the P wave changes depending upon the positioning or location of the electrode attached to the tip of the CVC. Normally as the electrode attached to the tip of the CVC moves from the SVC toward the sino-atrial node, the maximum value of the absolute value of the voltage of the P wave increases.

However, placement or location methods using P wave or other ECG waveform analysis have many disadvantages. For example, it is difficult to detect the exact location of the tip within last one-third of the SVC before the cavoatrial junction using this method. Accordingly, the final fixed position of the tip is not always optimal. Further, to identify the proper tip position, one must identify the point where the P wave is tallest; however, to identify the tallest P wave clinicians generally must "cross-the-line" by briefly entering the atrium (i.e., they must move beyond the point where the P wave is tallest to know where the tallest point is). This entry into the atrium is contrary to FDA regulations and causes additional and unnecessary risks for the patient. Also, successful placement of the CVC using this method ends up depending a great deal on the experience of the clinician, and is more difficult for less experienced clinicians. Another disadvantage of methods focused on analyzing P waves or other waveforms is that heart abnormalities, arrhythmias, anatomic variability, noise and artifacts may affect detection and interpretation of P-waves morphological changes.

Disclosed herein are new methods of objective assessment of the location of the catheter tip by analyzing ECG data point to point variability, which avoids the above disadvantages. The method evaluates the complexity of changes of an ECG signal to calculate the distance from the catheter tip to the cavoatrial junction. The method is based on chaos theory and the concept of self-organized criticality (SOC). Systems at critical transition point between chaos and order are said to be in a state of self-organized criticality. The concept of SOC may be applied in different areas such as biological systems, statistics, nature, and large electronic circuits.

SUMMARY OF THE INVENTION

Described herein are new methods and systems for endovascular device placement, and new methods and systems for assessing of the location of an endovascular device. In one embodiment, the method and system involves utilizing electrocardiogram (ECG) signal for positioning the tip of a device, e.g. a CVC, in vasculature.

In one embodiment, the method includes receiving time series data relating to intravascular ECG (ivECG) of the patient from a CVC placement device; measuring Proximity Index (PxI) using multiscale complexity analysis of ivECG time series of the patient; comparing the determined PxI with proximity thresholds related to distances from the CVC tip to cavoatrial junction; and providing an output indicative of position of the CVC tip in the SVC relative to the cavoatrial junction.

In one embodiment, a method of utilizing an ECG signal for positioning a tip of a central venous catheter (CVC)

includes receiving ivECG signal data, determining at least one PxI parameter, wherein the PxI parameter is a chaos theory complexity parameter associated with variability of the ivECG signal data. The method may also include comparing the at least one PxI parameter with a proximity threshold of a tip of the CVC to the cavoatrial junction, and providing an output indicative of proximity of the CVC tip to the cavoatrial junction.

In one embodiment, a method of positioning an endovascular device in vasculature, includes advancing an endovascular device into the vasculature, the endovascular device having an electrode for receiving ivECG signal data, receiving ivECG signal data using the electrode, and determining at least one PxI parameter based on the received ivECG signal data. The method may also include comparing the at least one PxI parameter with a proximity threshold indicating a location of the endovascular device in relation to a part of a patient's body, and providing an output indicative of proximity of proximity of the endovascular device to the part of the patient's body.

BRIEF DESCRIPTION OF THE DRAWINGS

The invention may be understood by reference to the following description taken in conjunction with the accompanying drawings, in which like reference numerals identify like elements, and in which.

Figure 1:
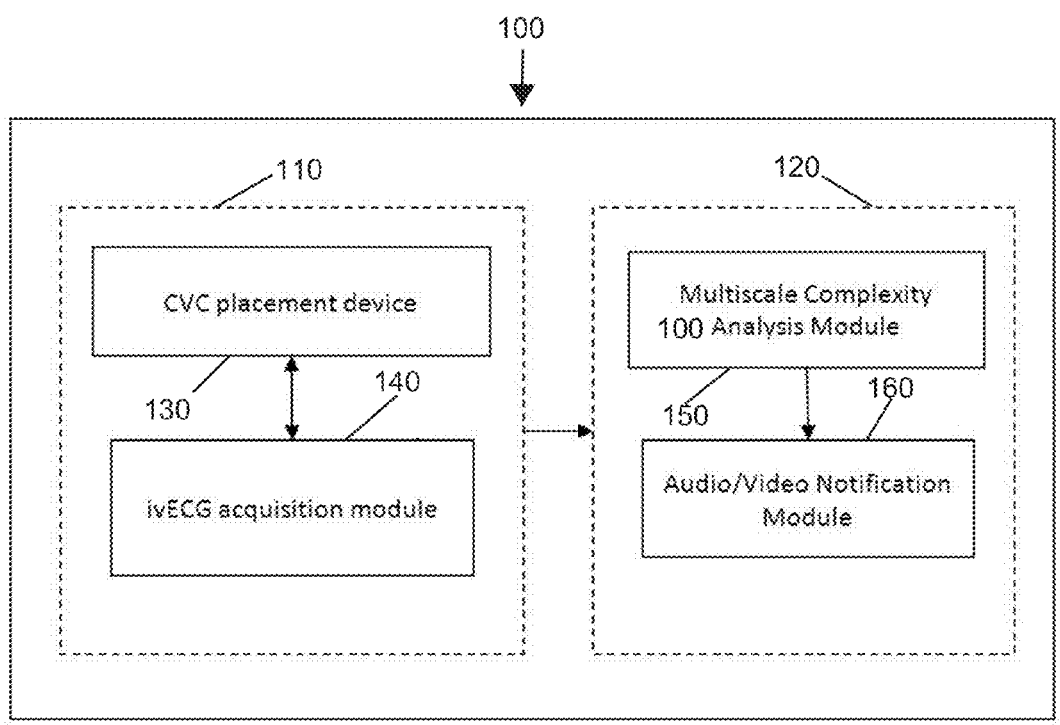
FIG. 1 shows a stylized diagram of a medical system that includes a CVC placement unit and a signal processing unit, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Described herein are methods and systems for endovascular device placement and assessing endovascular device location including features/steps believed to provide advantages over existing placement and location assessment methods and systems. Illustrative embodiments are described herein.

General methods and systems are described herein sufficient to enable one to develop a variety of implementations/applications without undue experimentation. In the development of particular applications, numerous implementation-specific decisions will be made to achieve the design-specific goals, which will vary from one implementation/application to another. It will be appreciated that such a development effort would be a routine undertaking for persons of ordinary skill in the art having the benefit of this disclosure.

This document does not intend to distinguish between components that differ in name but not function. In the following discussion and in the claims, the terms "including," "includes," "comprising," "have," and "has" are used in an open-ended fashion, and thus should be interpreted to mean "including, but not limited to." The word "or" is used in the inclusive sense (i.e., "and/or") unless a specific use to the contrary is explicitly stated.

In one embodiment, discussed in detail below, the present invention provides a system and method for positioning of a CVC tip in the SVC. While this system and method may be discussed in terms of placing a CVC tip in the SVC, the principles used in the system and method may be applied to a broader range of systems, methods, and devices. For example, the principles may be applied to implanting different types of catheters or devices (e.g., CVC, PICC, pacemaker leads, guiding guidewires) in the SVC or in selected veins and arteries other than, or in addition to, the SVC to achieve particular results.

As discussed in more detail below, the system and method evaluate the complexity of changes of an ivECG signal to calculate the position of an endovascular device, e.g., to calculate the distance from the tip of a CVC to the cavoatrial junction. The method is based on chaos theory and the concept of self-organized criticality (SOC).

FIG. 1 shows a simplified block diagram of an endovascular placement system in the form of a CVC placement system 100. CVC placement system 100 includes CVC placement unit 110 and signal processing unit 120. CVC placement unit 110 includes CVC placement device 130 and ivECG signal acquisition module 140. CVC placement unit 110 can be any type of endovascular device placement/confirmation system, e.g., any vein or artery catheterization or tip placement/confirmation system. For example, CVC placement unit 110 may be the Sherlock 3CG* Tip Confirmation System by Bard Access Systems, or a similar endovascular device placement system. The CVC placement unit 110 may include a variety of hardware and software used for inserting an endovascular device and sensing/acquiring signals related to device placement/confirmation. The CVC placement device 130 may include any components necessary to place the endovascular device. The ivECG signal acquisition module 140 may be a combination of hardware and software used to acquire a signal, e.g., an ivECG signal.

The signal processing unit 120 includes multiscale complexity analysis module 150 and PxI audio and/or visual notification module 160. The signal processing unit 120 utilizes the signal, e.g., the ivECG signal, acquired by the acquisition module 140 for the endovascular device positioning and confirmation. Multiscale complexity analysis module 150 may include software programmed for signal data processing. For example, multiscale complexity analysis module 150 may be programmed for processing ivECG signal data acquired from the acquisition module 140 to calculate PxI and/or the distance of the endovascular device from the cavoatrial junction, e.g., using the methods/algorithms discussed in more detail below. Audio and/or visual notification module 160 may include software that signals an associated device (e.g., a monitor, computer, audio device, and/or other display) to provide the user with an audio and/or visual indication/notification of PxI and/or the proximity of the endovascular device to the cavoatrial junction. The audio and/or visual notification may take a variety of forms, including as a graphical or numerical display of PxI, a graphical or numerical display of distance between the endovascular device and the cavoatrial junction, a graphical representation of the endovascular device moving relative to a graphical representation of the heart and/or SVC (e.g, a moving image of a CVC tip may be shown in an image of the SVC as it approaches the cavoatrial junction), a sound (e.g., a beep) that changes frequency as the endovascular device approaches the desired location, display colors may change as the endovascular device progresses (e.g., a red color may be displayed if the tip approaches to closely to the atrium), etc., and/or any combination of these.

Optionally, the signal processing unit 120 may be embedded in the CVC placement unit 110, for example, if the CVC placement unit 110 has a built in digital signal processing unit (DSP), e.g., as in the Sherlock 3CG* Tip Confirmation System. Alternatively, the signal processing unit 120 may utilize a separate DSP connected to CVC placement unit 110.

Figure 2:
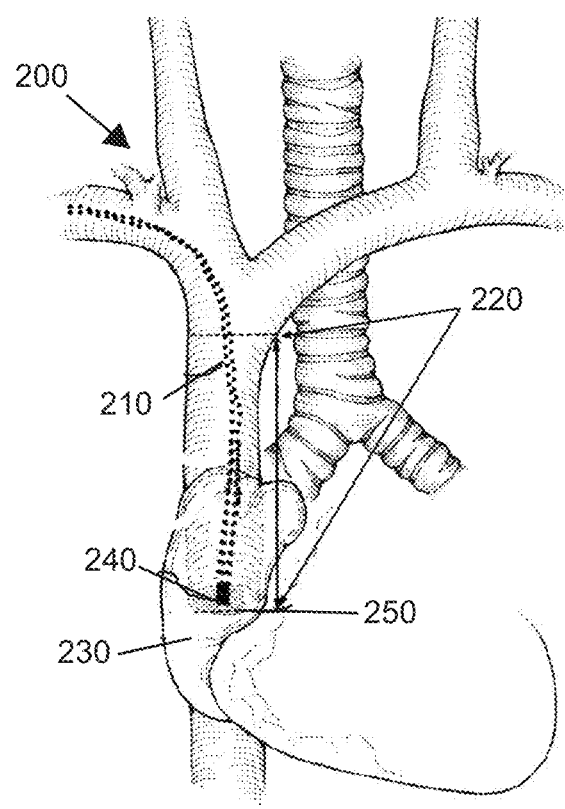
FIG. 2 shows the placement of a CVC in the SVC.

FIG. 2 shows a drawing of a heart 200 and surrounding vasculature. CVC 210 has an ivECG electrode type tip 240, and CVC 210 is shown placed in SVC 220 in an optimal position at the border 250 between the atrium 230 and SVC 220, i.e., the cavoatrial junction.

As shown in FIG. 2, a CVC 210 having an ivECG electrode tip 240 may be inserted into the vasculature or a blood vessel of a patient. CVC 210 is initially inserted into the patient's vasculature or blood vessel through a skin insertion site, e.g., an incision. Initial insertion may be done using an introducer. CVC 210 generally includes a proximal portion (not shown) that remains exterior to the patient and a distal potion that resides within the patient vasculature after placement is complete. The catheter proximal portion may include a hub that provides fluid communication between the one or more lumens of the CVC 210 and one or more extension legs extending from the hub.

Figure 3:
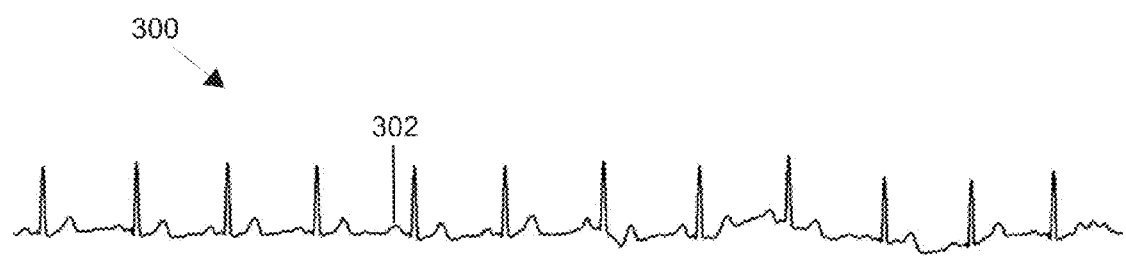
FIG. 3 shows a plotted ivECG time series recorded by an ivECG device.

As CVC 210 is inserted and advanced through the vasculature or blood vessel, the ivECG electrode tip 240 may be used to sense an ivECG signal of a patient. Accordingly, the ivECG electrode tip 240 may be part of CVC placement unit 110. It is noted that the CVC placement unit 110 may include and ivECG signal data of a patient may be gathered by many types of electrocardiographic devices, i.e., the ECG device used is not limited to one with one electrode located at the tip of a CVC. Further, the ECG device may include various components/features that work in combination, e.g., ivECG electrode tip 240 may function in combination with other features to detect the ivECG signal. FIG. 3 shows a representative ivECG waveform 300 acquired by an ECG device with a sense electrode located at the tip of the catheter, e.g., similar to CVC 110. FIG. 3 also shows a P wave 302.

The complexity of changes to an ECG signal, e.g., a signal similar to ivECG waveform 300, may be used to calculate the distance from the catheter tip to the cavoatrial junction. The method is based on chaos theory and the concept of self-organized criticality (SOC). Systems at critical transition point between chaos and order are said to be in a state of self-organized criticality. The concept of SOC may be applied in different areas such as biological systems, statistics, nature, and large electronic circuits. Many complex biological systems of interaction elements operate "on the edge of chaos," at a critical transition point between randomness and order. A chaotic system is characterized by 'unpredictability,' which simply means that one cannot predict how a system will behave in the future, on the basis of a series of observations over time. Systems on the edge of chaos are said to be in a state of Self-Organized Criticality (SOC). These systems are on the boundary between stable orderly behavior and unpredictable world of chaos. SOC emerges from studies of complex systems of interactive elements.

Dynamics of action potentials have a complex nature; accordingly, an ivECG signal has a complex nature. This complexity derives from interactions between several physiological variables, ANS and CNS regulation, hemodynamic forces, baroreceptor reflex, and others.

Takens' theorem states that it is possible to reconstruct a high dimensional system by observing a single output variable (F. Takens (1981). "Detecting strange attractors in turbulence." In D. A. Rand and L.-S. Young. Dynamical Systems and Turbulence, Lecture Notes in Mathematics, vol. 898. Springer-Verlag. pp. 366-381).

The methods of this disclosure may utilize ivECG data obtained by an electrocardiographic device (ECG device) as the single output variable of Takens' theorem. ivECG is an output of a complex cardiovascular system which operates in a state of SOC and follows the laws of chaos.

One method for the evaluation of complexity of high-dimensional, SOC systems, includes measuring the complexity of the system by using entropy. However, entropy-based or any other methods of measuring complexity at one scale may provide misleading results while assessing threshold levels of complexity, because data with different properties may produce vastly different results.

The method introduced herein uses Multiscale Complexity Analysis (MSCA) of dynamics of ivECG data using a Complementary Probability Cumulative Distribution Function, also called Tail Distribution, adapted for the analysis of dynamics of ivECG data. Tail Distribution is defined by the following equation (where P is the probability that the random variable X takes on a value more than x):

$$\overline{F}(x)=P(X>x)$$

An ECG device outputs the time series of ivECG data as a set of measured voltage amplitudes, $\{v_1,v_2,v_3, \ldots v_i,v_{i+1}, \ldots v_n\}$. ivECG time series is transformed to the time series of differences of successive points $\{d_1,d_2,d_3 \ldots d_i,d_{i+1}, \ldots d_{n-1}\}$ is the absolute difference, $|v_{i+1}-v_i|$ between successive points $v_{i+1}$ and $v_i$.

$P_i$ is the Probability in percentages that the absolute difference between the measured values of Successive Points is more than x.

$$P_i=P(d_i>x), \text{ where } d_i \text{ is } |v_{i+1}-v_i|$$

$P_i$ value at value $x=\alpha$ is the measurement of complexity at scale $\alpha$. Plotting $P_i$ values with x varying from 0 to maximum of $d_i$ provides a graph of multiscale complexity of ivECG dynamics. $P_i$ represents the tail distribution.

Figure 4:
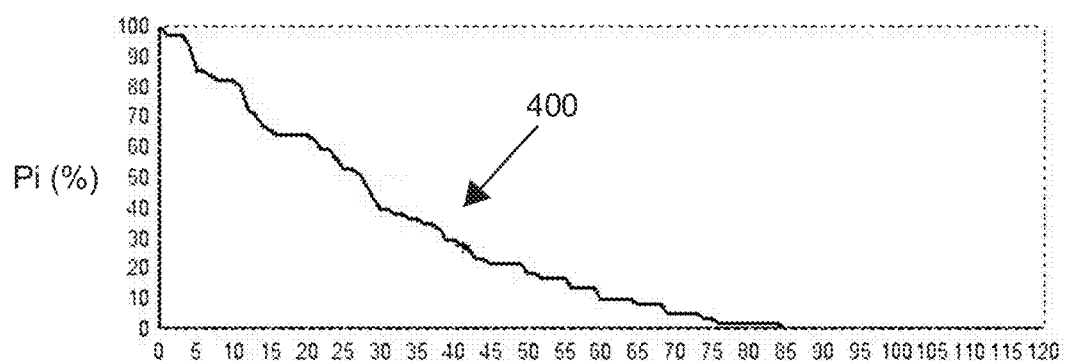
FIG. 4 illustrates a representative tail distribution graph for an ivECG time series.
Figure 5:
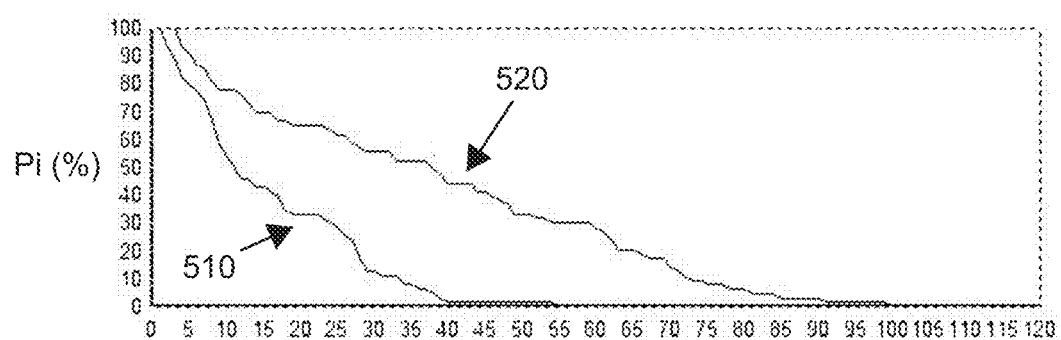
FIG. 5 shows tail distribution graphs of an ivECG time series at the entrance of the SVC and in close proximity to the cavoatrial junction.

FIG. 4 shows a graphical representation of the tail distribution 400 for the ivECG signal/time series 300 in FIG. 3. Whereas, FIG. 5 depicts a tail distribution curve 510 of another ivECG signal as measured at the entrance of the SVC, and a tail distribution curve 520 of ivECG signal as measured in close proximity to the cavoatrial junction. The tail distributions of various ivECG signals, e.g., as shown in FIGS. 3 and 4, may be calculated using the above equations. Referring again to FIG. 1, algorithms may be programmed into multiscale complexity analysis module 150 to perform these functions and calculate tail distributions for signals acquired by acquisition module 840.

Proximity Index (PxI) is calculated as a density of Tail Distribution Function (TDF) which is defined as $$TDF[a \leq x \leq b] = \int_a^b f(x)dx$$

For discrete values (e.g., discrete values of ivECG signal data) the equation becomes as follows (where max is an empirical cut off value representing maximal difference between the largest and smallest two consecutive values of $v_i$ and $v_{i+1}$):

$$TDF[0 \leq x \leq \max] = \sum_{i=0}^{max} p_i x_i$$

Figure 6:
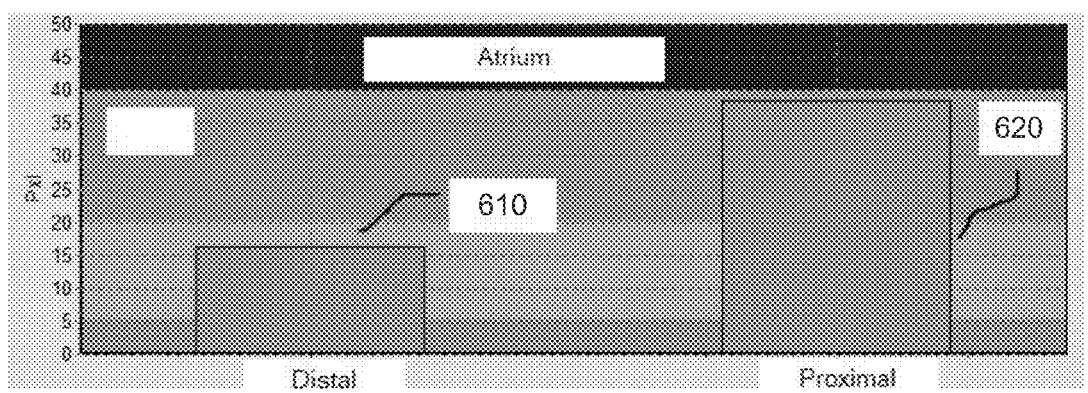
FIG. 6 illustrates the Proximity Index (PxI) or the density of the tail distribution shown in Fig. 5.
Figure 7:
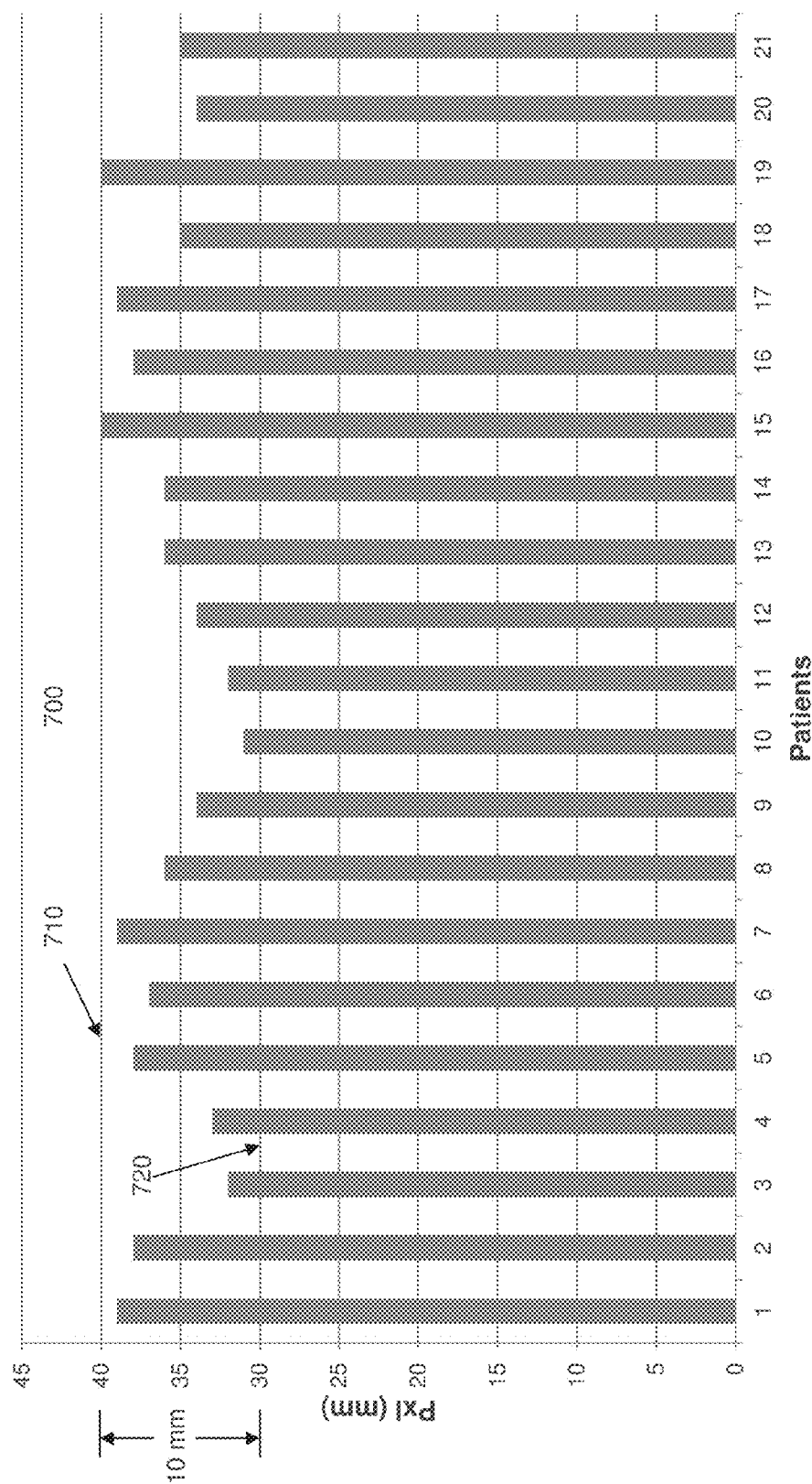
FIG. 7 shows PxI values for a group of 21patients.

FIG. 6 illustrates graphical representations of PxI values for the ivECG signals used to form the tail distributions of FIG. 5, including PxI value 610 of the ivECG signal measured at the entrance of the SVC, and PxI value 620 of the ivECG signal measured in close proximity to the cavoatrial junction. FIG. 7 shows a graphical representation 700 of actual PxI values for the tip confirmation of 21 patents. All placements of the CVC tip are within 10 mm from the cavoatrial junction as represented by the dotted line 710 at the nominal value 40 of PxI. In other words, the PxI values for each patient are above the proximity threshold shown by dotted line 720. When the PxI values cross the proximity threshold 720 at the nominal value of 30 PxI, this indicates that the tip of the CVC catheter is within the 10 mm of the cavoatrial junction. If the PxI values crossed threshold 710, this would indicate that the tip of the CVC catheter has passed the cavoatrial junction and entered the atrium. Using this method of analysis a clinician does not need to "cross-the-line" or enter the atrium to know when the tip is correctly placed. PxI values of various ivECG signals, e.g., as shown in FIGS. 6 and 7, may be calculated using the above equations. Referring again to FIG. 1, algorithms may be programmed into multiscale complexity analysis module 150 to perform these functions and calculate PxI and correlate PxI to distance between the endovascular device and the cavoatrial junction, e.g., the distance between the tip of a CVC and the cavoatrial junction.

Figure 8:
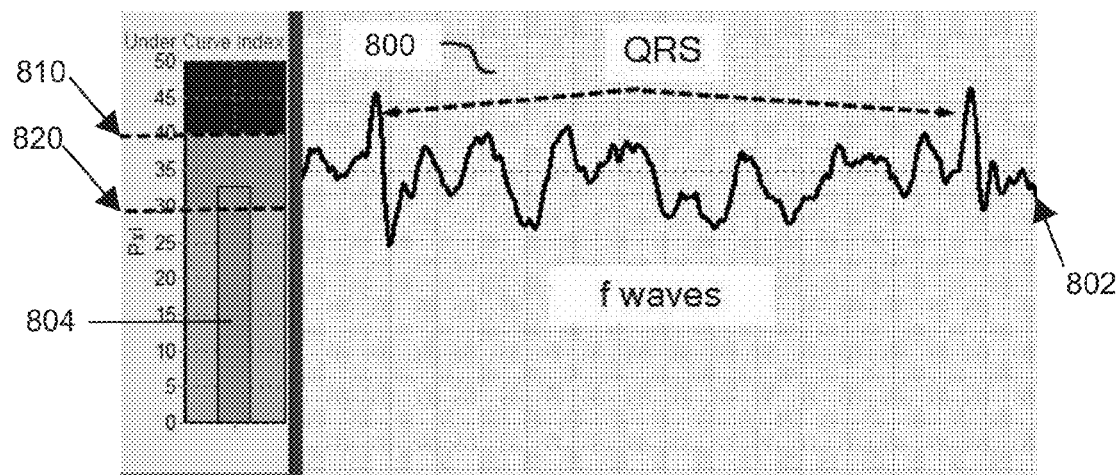
FIG. 8 shows a PxI value for a patient with atrial fibrillation and a corresponding ivECG time series.

FIG. 8 illustrates the CVC tip confirmation 800 for a patient with atrial fibrillation. The ivECG signal data 802 for the patient is shown on the right, and the PxI value 804 calculated from this signal data is shown on the left. A proximity threshold 820 signaling the point at which the tip is within 10 mm of the cavoatrial junction and a threshold 810 signaling the point at which the tip is at the cavoatrial junction are also shown. As shown in the ivECG signal data 802 of FIG. 8, P wave analysis is impossible during atrial fibrillation, e.g., because P waves are absent or distorted. This can be seen by comparing the signal data 802 of FIG. 8 with the signal data 300 and P wave 302 of FIG. 3. Accordingly, methods using assessment of morphological changes of P waves of ivECG are not applicable for patients with atrial fibrillation. In contrast, the above method of placing an endovascular device or assessing location of an endovascular device using multiscale complexity analysis and identifying PxI and comparing it with a proximity threshold is unaffected by atrial fibrillation. Accordingly, the disclosed method allows for accurate placement of the endovascular device even in cases of atrial fibrillation.

All of the methods disclosed and claimed herein may be made and executed without undue experimentation in light of the present disclosure. While the methods of this invention have been described in terms of particular embodiments, it will be apparent to those skilled in the art that variations may be applied to the methods and in the steps, or in the sequence of steps, of the method described herein without departing from the concept, spirit, and scope of the invention, as defined by the appended claims. It should be especially apparent that the principles of the invention may be applied to selected veins and arteries other than, or in addition to, the SVC to achieve particular results.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. A method of utilizing an ECG signal for positioning a tip of a central venous catheter (CVC) comprising:
   receiving ivECG (intravascular ECG) signal data;
   determining at least one PxI (proximity index) parameter, wherein the PxI parameter is a chaos theory complexity parameter associated with variability of the ivECG signal data;
   comparing the at least one PxI parameter with a proximity threshold of a tip of the CVC to a cavoatrial junction; and
   providing an output indicative of proximity of the CVC tip to the cavoatrial junction.

2. The method of claim 1, wherein the at least one PxI parameter is a density of a tail distribution.

3. The method of claim 2, wherein the tail distribution is a probability that a random variable X takes on a value more than x.

4. The method of claim 3, wherein the random variable X belongs to a time series of differences of successive points $\{d_1, d_2, d_3, \ldots d_i, d_{i+1}, \ldots d_{n-1}\}$ where $d_i$ is an absolute difference, $|v_{i+1} - v_i|$ between successive points $v_{i+1}$ and $v_i$ of the ivECG signal data.

5. The method of claim 4 wherein the x is variable from 0 to maximal value $d_i$ from the time series $\{d_1, d_2, d_3, \ldots d_i, d_{i+1}, \ldots d_{n-1}\}$.

6. A method of positioning an endovascular device in vasculature, comprising:
   advancing the endovascular device into the vasculature, the endovascular device having an electrode for receiving ivECG (intravascular ECG) signal data;
   receiving ivECG signal data using the electrode;
   determining at least one PxI (proximity index) parameter based on the received ivECG signal data;
   comparing the at least one PxI parameter with a proximity threshold indicating a location of the endovascular device in relation to a part of a patient's body; and
   providing an output indicative of proximity of the endovascular device to the part of the patient's body.

7. The method of claim 6, wherein the endovascular device is a central venous catheter having a tip, and advancing an endovascular device into the vasculature includes advancing the central venous catheter into the vasculature, the central venous catheter having an electrode for receiving ivECG signal data.

8. The method of claim 7, wherein providing an output includes providing an output indicative of proximity of the tip of the central venous catheter to a cavoatrial junction of the patient's body.

9. The method of claim 8, wherein the determining at least one PxI parameter based on the received ivECG signal data and the comparing the at least one PxI parameter with the proximity threshold are done using a multiscale complexity analysis module including software programmed for processing the ivECG signal data.

10. The method of claim 6, wherein the at least one PxI parameter is a density of tail distribution.

11. The method of claim 10, wherein the tail distribution is a probability that a random variable X takes on a value more than x.

12. The method of claim 11, wherein the random variable X belongs to a time series of differences of successive points $\{d_1, d_2, d_3, \ldots d_i, d_{i+1}, \ldots d_{n-1}\}$ where $d_i$ is an absolute difference, $|v_{i+1}-v_i|$ between successive points $V_{i+1}$ and $v_i$ of the ivECG signal data.

13. The method of claim 12 wherein the x is variable from 0 to maximal value $d_i$ from the time series $\{d_1, d_2, d_3, \ldots d_i, d_{i+1}, \ldots d_{n-1}\}$.

14. The method of claim 6, wherein the output indicative of proximity of the endovascular device to the part of the patient's body is a graphical output shown on a display.

15. A medical system for endovascular device placement comprising:
 a placement unit including a signal acquisition module and an electrode for acquiring ivECG (intravascular ECG) signal data;
 a multiscale complexity analysis module including software programmed for processing the ivECG signal data acquired by the signal acquisition module;
 a device configured to provide an audio and/or visual indication of PxI (proximity index) and/or a proximity of the endovascular device to a part of a patient's body;
 an audio and/or visual notification module programmed to signal the endovascular device to provide a user with an audio and/or visual indication of PxI and/or the proximity of the endovascular device to the part of the patient's body.

16. The medical system of claim 15, wherein the endovascular device is a central venous catheter and the part of the patient's body is the cavoatrial junction of the patient's body.

17. The medical system of claim 15, wherein the software of the multiscale complexity analysis module is programmed to determine at least one PxI value based on the ivECG signal data acquired by the signal acquisition module.

18. The medical system of claim 17, wherein the software of the multiscale complexity analysis module is programmed to compare the at least one PxI value with a proximity threshold and provides this information to the audio and/or visualization notification module.

19. The medical system of claim 18, wherein the audio and/or visualization notification module is programmed to signal the endovascular device to provide the user with an audio and/or visual indication of PxI and/or the proximity of the endovascular device to the part of the patient's body based on the comparison of the at least one PxI value with the proximity threshold.

* * * * *